United States Patent
Bannenberg et al.

(10) Patent No.: US 12,352,688 B2
(45) Date of Patent: Jul. 8, 2025

(54) OPTICAL THIN-FILM HYDROGEN SENSING MATERIAL BASED ON TANTALUM OR OTHER GROUP V ELEMENT ALLOY

(71) Applicant: TECHNISCHE UNIVERSITEIT DELFT, Delft (NL)

(72) Inventors: Lars Johannes Bannenberg, Delft (NL); Herman Schreuders, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 198 days.

(21) Appl. No.: 18/251,494

(22) PCT Filed: Oct. 28, 2021

(86) PCT No.: PCT/NL2021/050658
§ 371 (c)(1),
(2) Date: May 2, 2023

(87) PCT Pub. No.: WO2022/098230
PCT Pub. Date: May 12, 2022

(65) Prior Publication Data
US 2024/0011897 A1    Jan. 11, 2024

(30) Foreign Application Priority Data
Nov. 3, 2020 (NL) .................................. 2026815

(51) Int. Cl.
*G01N 21/31* (2006.01)
*G01N 33/00* (2006.01)
*C01B 3/00* (2006.01)

(52) U.S. Cl.
CPC .......... *G01N 21/31* (2013.01); *G01N 33/005* (2013.01); *C01B 3/0031* (2013.01)

(58) Field of Classification Search
CPC ... G01N 21/31; G01N 21/7703; C01B 3/0031
See application file for complete search history.

(56) References Cited

U.S. PATENT DOCUMENTS

| | | | |
|---|---|---|---|
| 7,370,511 B1 * | 5/2008 | Chen | G01N 33/005 73/31.05 |
| 2017/0023475 A1 | 1/2017 | Dam et al. | |

FOREIGN PATENT DOCUMENTS

| | | | | |
|---|---|---|---|---|
| EP | 2594937 A1 * | 5/2013 | | G01N 33/005 |
| EP | 2988116 A1 | 2/2016 | | |
| EP | 3385702 A1 | 10/2018 | | |

(Continued)

OTHER PUBLICATIONS

C. Perrotton et al., "A distributed optical fiber sensor for hydrogen detection based on Pd, and Mg alloys", Proc. of SPIE, vol. 7675, 2010, Pp. 76750F-1-76750F-8.
(Continued)

*Primary Examiner* — Maurice C Smith
(74) *Attorney, Agent, or Firm* — AEON Law, PLLC; Adam L. K. Philipp; Charlotte E. Holoubek

(57) ABSTRACT

The present invention relates to a tuneable hydrogen sensing device, to a method for producing said thin-film device, to a use of said thin-film device for detecting a chemical species, to a sensor, such as a hydrogen sensor, to a device comprising said sensor, and to an apparatus for detecting hydrogen.

19 Claims, 4 Drawing Sheets

(56) References Cited

FOREIGN PATENT DOCUMENTS

WO  2015080577 A1  6/2015

OTHER PUBLICATIONS

Figure 1:
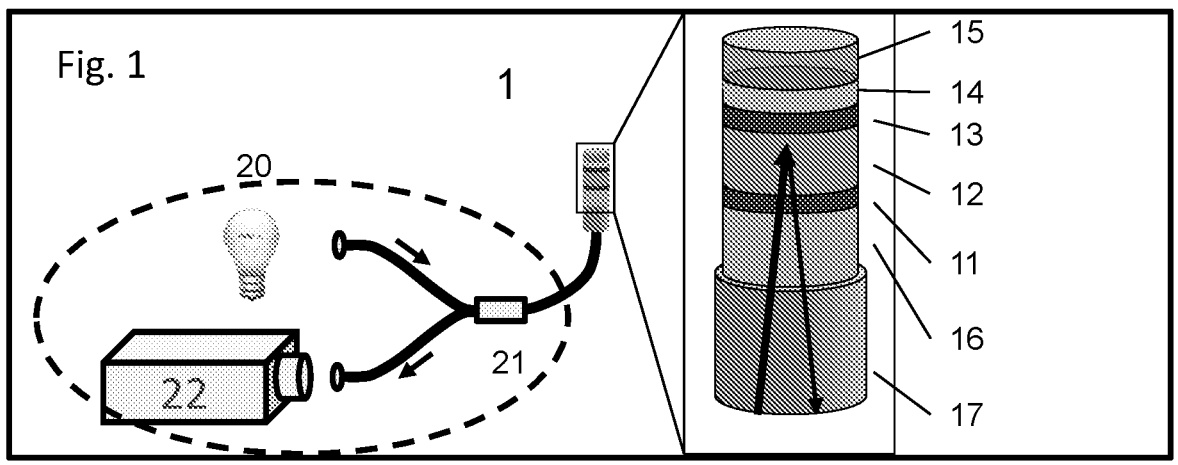

International Search Report and Written Opinion received for PCT Patent Application No. PCT/NL2021/050658, dated Jan. 20, 2023, 17 pages.
Westerwaal et al., "Thin film based sensors for a continuous monitoring of hydrogen concentrations", Sensors and Actuators B: Chemical, vol. 165, No. 1, 2012, pp. 88-96.

* cited by examiner

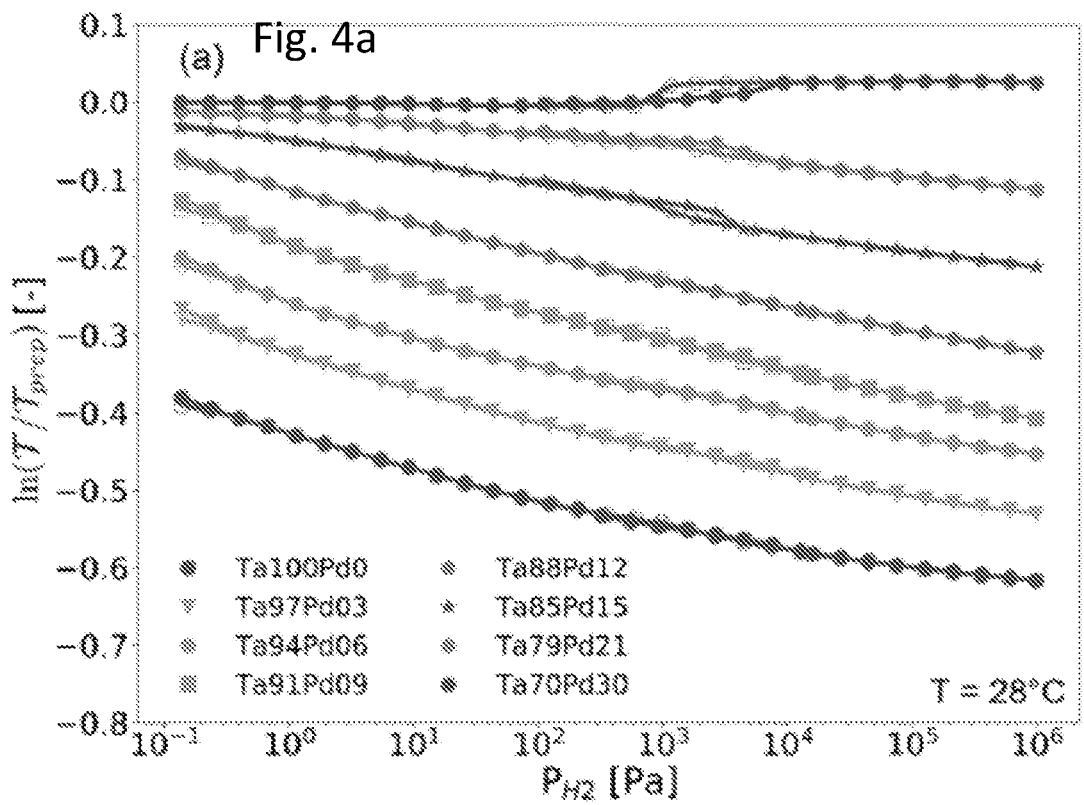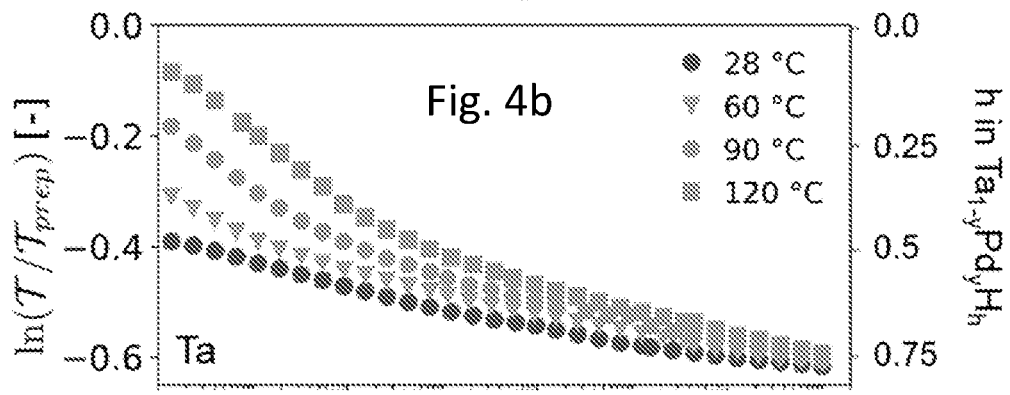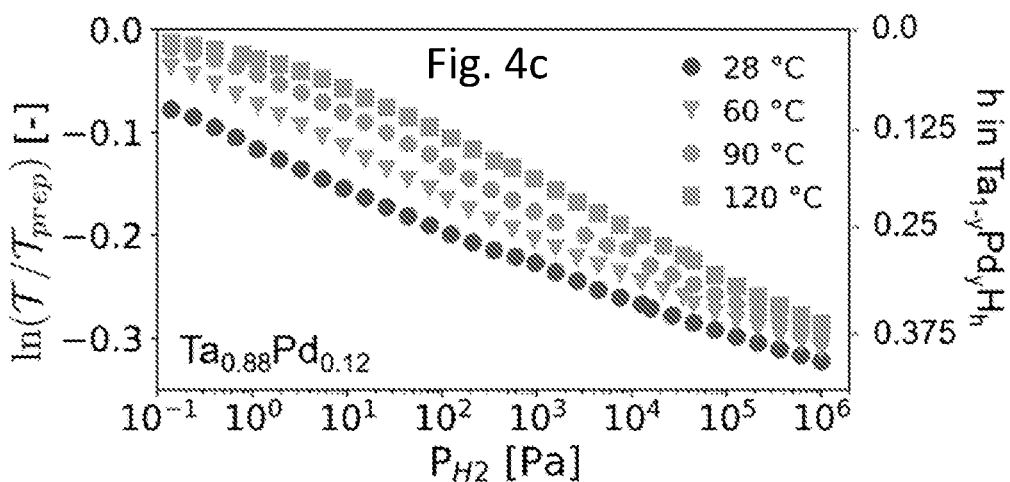

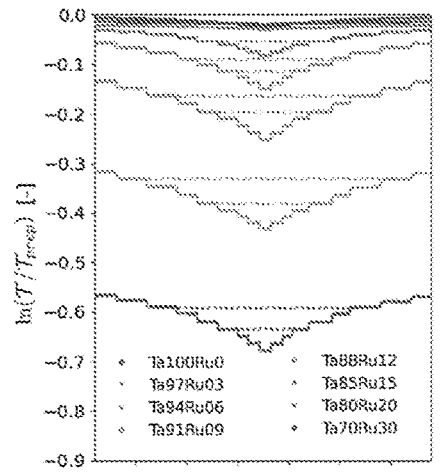
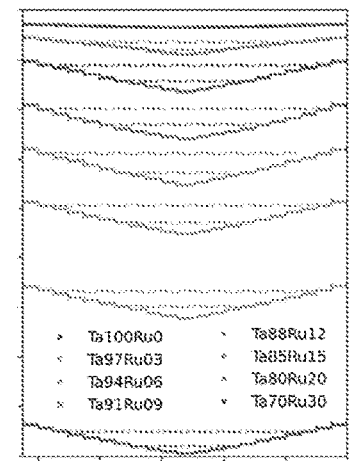
Fig. 5a  Fig. 5b  Fig. 5c
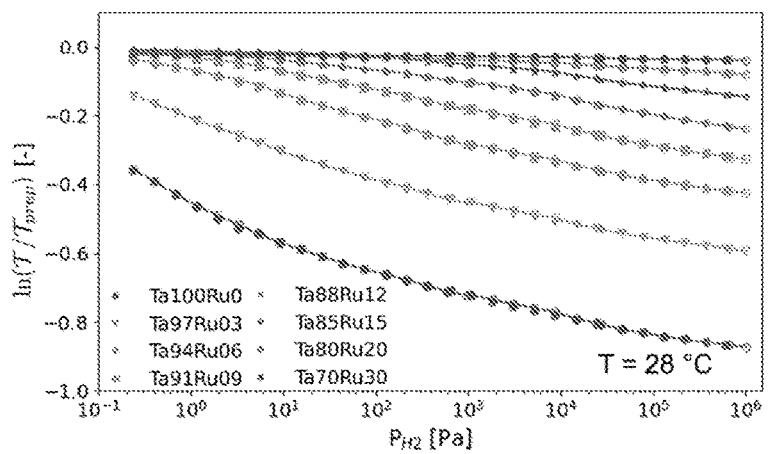
Fig. 6

OPTICAL THIN-FILM HYDROGEN SENSING MATERIAL BASED ON TANTALUM OR OTHER GROUP V ELEMENT ALLOY

RELATED APPLICATIONS

This application is a national entry of PCT International Patent Application No. PCT/NL2021/050658, filed Oct. 28, 2021, in the name of "TECHNISCHE UNIVERSITEIT DELFT" [NL], which PCT application claims the benefit of priority of Netherlands Patent Application Serial No. 2026815, filed Nov. 3, 2020, in the name of "TECHNISCHE UNIVERSITEIT DELFT" [NL]. The entire contents of the above-referenced applications and of all priority documents referenced in the Application Data Sheet filed herewith are hereby incorporated by reference for all purposes.

FIELD OF THE INVENTION

The present invention relates to a tuneable hydrogen detecting device, to a method for producing said thin-film device, to a use of said thin-film device for detecting a chemical species, to a sensor, such as a hydrogen sensor, to a device comprising said sensor, and to an apparatus for detecting hydrogen.

BACKGROUND OF THE INVENTION

In a more generic perspective in an economy with hydrogen as a major energy carrier, the development of affordable, reliable, sensitive and selective hydrogen sensors is indispensable. Several types of hydrogen sensors are currently available, which exploit one or more of the following detection mechanisms: catalytic, electrochemical, mechanical, optical, acoustic, thermal conductivity, resistance and work function. Since hydrogen detection often takes place in an explosive environment, cf. for leak detection or for hydrogen-concentration measurements in gas streams, use of optical hydrogen sensors has a major advantage of being intrinsically safe due to the lack of electric leads in the sensing area.

The term "alloy" is used to describe a mixture of atoms. Therein a primary constituent is a metal. This primary constituent is first mentioned. The primary metal may be referred to as the base, the matrix, or the solvent. The secondary (and further) constituents are often called solutes. If there is a mixture of only two types of atoms it is called a binary alloy. If there are three types of atoms it is called a ternary alloy, etc. When refer-ring to an alloy one typically uses the primary atom, e.g. a Mg-alloy comprises Mg as primary atom. In view of the primary atom forming the matrix, one can not permutate the order of elements of an alloy, as then the nature of the alloy would change, in this case from one metal to another. Put different, a Mg-alloy is not a Ca alloy, even if the Mg-alloy would comprise Ca as a further constituent.

In principle, Pd-based optical fibre sensors meet certain requirements to a hydrogen sensor. Palladium has some attractive properties such as the ability to dissociate hydrogen at room temperature and a modest sensing range of about three orders of magnitude in pressure. However, the first-order transition from the dilute $\alpha$-$PdH_x$ to the higher hydrogen concentration metal-hydride $PdH_x$ $\beta$-phase that occurs upon hydrogenation causes the optical response to be non-linear, i.e. depending strongly on pressure, and highly hysteretic. Furthermore, this transition induces relatively long response times of Pd. To overcome these serious issues, alloys of Pd with elements including Au, Ag and Cu have been considered. These alloys have the advantage that the abovementioned first order phase transition may be eliminated, however, the alloying also dramatically de-creases the optical contrast and thus diminishes the sensitivity of the sensor. In addition, different from other geometries as e.g. nanoparticles, in thin films, which are typically much cheaper and easier to manufacture, hysteresis arising from the expansion of the film upon hydrogenation and the clamping of the film to the support remains present. In addition, the response times to hydrogen for such Pd-based thin-film sensors are too long for most applications.

So such sensing devices are known from the prior art. As an example, WO2007/126313 A1 discloses a switchable mirror device comprising an active layer, wherein said active layer changes its optical properties upon addition or removal of hydrogen and comprises a hydrogen and oxygen permeable and water impermeable layer, wherein said layer is liquid water impermeable and water vapour permeable and has hydrophobic surface properties.

In a further example, WO2007/049965 A1, an optical switching device is recited. In such a device auxiliary layers may be present, such as for protection. Such layers typically are rather thick.

Some prior art recite hydrogen sensors. EP 3 385 702 (A1) recites an optical gas sensing system for sensing hydrogen in a fluid is provided. The system comprises an optical sensor comprising a fiber, the fiber including at an end portion a sensor element with a sensing layer configured to change its dielectric properties depending on a gas partial pressure at the sensing layer; the sensing layer comprises a thin film of a metal alloy, wherein the alloy comprises Mg, Ni, and a component M, wherein M is at least one of Zr, Ta, and Hf. The alloy has the composition $Mg_xNi_yM_z$, wherein x is from 40 to 59, y is from 10 to 40, and z is from 10 to 40, in combinations where the numbers add up to 100. Other (non-limiting) suitable materials for the sensing layer are Mg—Ti alloys, and Y alloys. EP 2 988 116 A1 recites an optical sensor for detecting hydrogen in a fluid in physical contact with the sensor. The sensor comprises an optical fiber, wherein an end portion of the optical fiber is coated with a multilayer comprising a film of an alloy, the alloy comprising Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40, and a catalyst layer comprising Pd. WO 2015/080577 A1 recites a hydrogen sensor with an alloy $A_xB_yC_z$, with A being selected from alkaline earth-metals (Group II), preferably from Mg, and Ca, B being selected from Zr, Hf, Nb, Y, La, and Ta, preferably Zr, Hf and La, and C being selected from a period 4 transition metal (Sc, Ti, V, Cr, Mn, Fe, Co, Ni, Cu and Zn), preferably Sc, Ti, Ni and V, with ranges preferably as follows: $x \in [0.1$-$0.95]$, $y \in [0.1$-$0.4]$, $z \in [0.05$-$0.6]$, and preferably y: $x \in [0.7$-$0.9]$. Perroton et al. in "A distributed optical fiber sensor for hydrogen detection based on Pd, and Mg alloys", Proceedings of SPIE, Vol. 7675, Apr. 19, 2010, p. 76750F-76750E-8 recites in fact a PdH alloy, or likewise a $Mg_{70}Ti_{30}$ alloy (with a Pd-catalyst layer). So these documents relate to Mg-alloys, Ca-alloys, Mg—Ti alloys and Y alloys. Westerwaal et al. in "Thin film based sensors for a continuous monitoring of hydrogen concentrations", SENSORS AND ACTUATORS B: CHEMICAL, Elsevier, Vol. 165, No. 1, (2012), p. 88-96, recite a sensor comprising $Pd_{95}Ta_5$, $Pd_{95.3}Ta_{4.7}$, $Pd_{96.1}Ta_{3.9}$, $Pc_{97.3}Ta_{2.7}$. This is a Pd-alloy. US 2017/023475 A1 recites a single element thin-film device, for detecting hydrogen absorption. A single element is not an alloy. The single elements are selected from the group consisting of Hf, Ta, Ti, Zr, V, and Nb. The inventors published a scientific article relating to Metal Hydride Based Optical Hydrogen Sensors in Journal of the Physical Society of Japan 89, 051003 (2020). This article provides an overview of thin film metal hydrides used as optical sensors.

The present inventors further developed hydrogen sensors, aiming at tuning a detection level with a wide sensing-range of hydrogen pressures.

The present invention therefore relates to a tuneable hydrogen sensing device and further aspects thereof, which overcomes one or more of the above disadvantages, without compromising functionality and performance.

SUMMARY OF THE INVENTION

It is an object of the invention to overcome one or more limitations of the thin-film devices of the prior art and at the very least to provide an alternative thereto. The present thin film metal hydride based optical hydrogen sensors provide an attractive option to sense hydrogen in a variety of conditions and have an attractive safety benefit over other methods of detection: They do not require the presence of electrical leads near the sensing area. These sensors rely on a change of the optical properties arising from a change in the hydrogenation of the metal hydride sensing layer in response to a different partial hydrogen pressure in the environment of the sensor. The response, depending on the hydrogen pressure, can be well within one second, such as within 0.1 second. Also the present thin-film device is very stable over time.

Performance and characteristics of an optical hydrogen sensor are found to relate to the material properties of the metal hydride sensing layer. Inventors show that the exemplary present thin-film $Ta_{1-y}Pd_x$ is an effective optical sensing materials with extremely wide sensing ranges of at least seven orders of magnitude in hydrogen pressure within a single thermodynamic phase. The nanoconfinement of the exemplary $Ta_{1-y}Pd_x$ sup-presses the first-order phase transitions present in bulk and ensures a sensing response free of any hysteresis. Unlike other sensing materials, exemplary $Ta_{1-y}Pd_x$ features the special property that the sensing range can be easily tuned by varying the Pd concentration without a reduction of the sensitivity of the sensing material. Optionally combined with a suitable capping layer, sub-second response times can be achieved even at room temperature, faster than any other known thin-film hydrogen sensor. The combination of the superior sensing characteristics, the relatively easy and cheap manufacturing of the thin films and the simple and safe optical read out make the present sensing material particularly suited for large-scale implementation in tomorrow's hydrogen economy. The present invention is also topic of a submitted scientific article by the inventors Bannenberg, L. J., Schreuders, H., Dam, B., Tantalum-Palladium: Hysteresis-Free Optical Hydrogen Sensor Over 7 Orders of Magnitude in Pressure with Sub-Second Response. Adv. Funct. Mater. 2021, 31, 2010483. Available at doi.org/10.1002/adfm.202010483, which article and its contents is incorporated by references.

The present tuneable hydrogen sensing device may be combined with a capping layer of e.g. $Pd_{0.6}Au_{0.35}Cu_{0.05}$ covered with e.g. a 30 nm polytetrafluoroethylene (PTFE) protective layer, it already features a sub-second response at room temperature in a pressure range of $10^{+2} < PH_2 < 10^{+5}$, i.e. a concentration of 0.1 to 100% under ambient conditions. Together with the high and almost constant sensitivity over the entire sensing range of seven orders of magnitude in pressure, the $Ta_{1-y}Pd_y$ based thin film sensor meets the most stringent criteria set for hydrogen sensors by the U.S. Department of Energy.

In a first aspect, the invention relates to a tuneable thin-film hydrogen sensing device according to claim 1, comprising a hydrogen sensing material, the hydrogen sensing material comprising an alloy $M_{1-y}A_xB_z$, wherein y=x+z, and wherein B is optionally present, wherein the metal M is selected from Group V elements, and at least one alloying element A, and at least one alloying element A being selected from elements with a cubic unit cell, such as Pd, Ni, Pt, Ru, Rh, Al, V, Cr, Mn, Fe, Cu, Si, Ge, Nb, Ag, Yb, Ta, W, Ir, Au, Pb, Sn, and combinations thereof, wherein the hydrogen equilibrium pressure is tuneable by changing an amount x of the at least one alloying element in the alloy $M_{1-y}A_xB_z$ wherein the alloying element A is present in an amount of 0.01-35 atom %, typically 1-30 atom %, such as 3-24 atom %. The inventors have found a way to measure in a controlled and reliable, hysteresis free, manner an amount of hydrogen, such as in an environment wherein the device is place. Therewith a maximum sensing range is ex-tended from $10^{-1}$ Pa (0.001 mbar), which is actually the lowest feasible hydrogen pressure that can be provided in laboratory conditions, to $10^8$ Pa (1,000,000 mbar), which is actually in the order of the highest pressure that can be achieved under said laboratory conditions, at a temperature of 20° C. The device is capable of detecting a hydrogen concentration and likewise a hydrogen pressure, such as by a change in optical properties of the sensing material.

The present device can measure an amount of hydrogen, e.g. as a concentration and as a (partial) pressure. A further advantage is that (only) one hydrogen sensing material can be used as a sensing layer, thus making the device simple and cheaper to produce. Typically the alloy has reversible phase transitions or no phase transitions upon hydrogenation, which is an advantage. The present sensing material can comprise hydrogen in an amount of [transition metal (TM)]:[H] of [1,2]. For example an amount of hydrogen in Ta can be up to TaH, whereas with Nb and V it can be up to $NbH_2$ and $VH_2$, respectively. It is noted that alloying in general, such as with Pt, and Ni, may reduce a maximum amount of hydrogen that the sensing material can comprise.

The present thin film device provides over a large range of hydrogen concentrations (at least 7 orders of magnitude) and at low hydrogen concentrations (levels as low as a few ppm at room temperature, typically a temperature of 25° C.-35° C.) a one-to-one response (during loading and unloading), such as in at least the visible/near-infrared part of the spectrum, which response is tuneable in terms of an operating range. The large range may further provide the advantage of requiring only one (or two) sensors to monitor a hydrogen pressure, instead of a range of sensors. A further advantage is that segregation, typically being an optional failure mode in multiple elements hydrogen sensors, is not observed for the present device, such as the Y—Zr hydrogen sensor, enabling a long-life and stable performance of the sensor.

The present device therefore provides a well-defined relation between a hydrogen concentration and material response (in e.g. the optical sensing layer). As the mechanism of absorption is in principle reversible, also controlled and reliable desorption is provided. As such the present device is capable of monitoring fluctuations in hydrogen concentration.

In an example a means for monitoring a (varying) hydrogen concentration over a large range of pressures is provided. It is noted that the present optical system is much safer and more reliable to use and to handle compared to e.g. electrical (conducting) sensors, especially in environments where a large electro-magnetic field or a relatively large hydrogen concentration may be present.

In addition to the sensing material (20) a hydrogen sensing material read-out system is provided, wherein the read-out system is selected from optical read-out systems, dielectric read-out systems, electro-magnetic read-out systems, such as an electrical cur-rent detector, an electrical voltage detector, an electrical resistance detector, and a transistor, and combinations thereof. It is noted that the present hydrogen sensing material changes properties when the hydrogen content therein changes. This change in properties can be measured by a read-out system. Albeit inventors focused on optical read-out systems, all the aforementioned could be used, in principle equally well.

In a second aspect the present invention relates to a method for producing a tuneable hydrogen sensing device comprising providing a substrate, (co)depositing a sensing layer on the substrate, the sensing layer comprising a metal, and at least one alloying element, wherein the at least one alloying element is present in an amount of 0.1-35 atom %, optionally providing a capping layer, preferably comprising Pd and Au and optionally Cu, optionally providing a protective layer, if present on the capping layer, and optionally cycling the device 1-10 times before use, e.g. to settle the microstructure of the sensing material. It has been found experimentally that for a stable performance a device is first cycled at least once, and sometimes a few times, from a relatively low (hydrogen) pressure to a relatively high (hydrogen) pressure, and back. 1-7 cycles are typically sufficient, such as 1-3 cycles.

The present device is also considered for use in detecting a chemical species other than hydrogen, typically relatively simple chemical species, such as oxygen, nitrogen, carbon monoxide, carbon dioxide, etc. especially for detecting a large range of concentrations thereof.

In a further aspect the present invention relates to a sensor comprising at least one device of the present invention, comprising an optical transmitter, such as an optical fibre, wherein the sensing layer is located at a top of the optical transmitter and/or wherein the sensing layer is located at a longitudinal side of the optical transmitter.

A further application relates to the detection of hydrogen in devices, such as power transformers, a hydrogen storage device, and batteries, by means of optical fibres, where the concentration of hydrogen (in oil) is considered indicative for aging of the insulation oil.

Another application relates to detection of (small) leaks. Hydrogen gas—as the smallest molecule—can be used to test presence of small leaks. By means of optical fibres, the present sensing material is used to detect small leaks. Such detection can take place over a long period of time, and in small areas which are difficult to reach.

In an example an apparatus for detecting hydrogen is provided, comprising a sensor, the sensor being located at a longitudinal side of an optical transmitter, or at a top side of an optical transmitter, the optical transmitter comprising a central transmitting element, such as a quartz core, a tuneable hydrogen sensing device according to the invention, and a spectrometer.

A person of skill in the art is able to identify many suitable substrate materials upon which a thin-film device such as the thin-film device of the invention can be constructed. Examples of suitable substrate materials include glass, quartz, indium-tin oxide, etc. The substrate material is preferably optically transparent (more than 95%), at least over a proportion of the visible, UV and/or IR regions of the electromagnetic spectrum (200 nm-12000 nm). Such provides for use of white light, IR-light, UV-light, a laser with a specific wavelength, and combinations thereof.

As mentioned above, optical sensing layers, with variable optical properties depending on e.g. a hydrogen content of the layer, e.g. comprising an alloy, are known in the prior art. In an example of the present invention the sensing layer is the present alloyed metal.

The optical sensing layer may be in a sequence of layers, or layer stacks, or a continuously changing layer, or in 2- or 3-dimensional domains, or combinations thereof.

A catalyst such as in a layer may be provided on top of the optical sensing layer, such as coating the optical sensing layer. Examples of such layers include for example Pd-layers. The Pd-layers may comprise pure Pd or mixtures comprising Pd. For example, Au can be added in a quantity of for example 20-30 mole %. The catalyst may also relate to a complex layer, suited for the present purpose. Such layers serve to facilitate hydrogen absorption by the optical sensing layer.

It is noted that a term as "on top" may relate to a sequence of e.g. layers, a first layer coating a second layer, a layer provided on an intermediate layer, the intermediate provided on e.g. the sensing layer, etc. The layer may also partly be on top. In view of the present application such terminology is mainly functional of nature.

On top of the optical sensing layer, or where present, on top of the catalyst (layer), a protective layer is provided, the protective layer not limiting functionality of the optical sensing layer, e.g. being permeable to relevant species, and protecting the optical layer. Both the catalyst layer (where present) and the protecting layer are permeable to a species to be measured, such as hydrogen, and are optically transparent, at least over a range of the visible, UV and/or IR regions of the electromagnetic spectrum. An example of a protecting layer from the aforementioned WO2007/126313 A1 is to provide a layer of PTFE. The protective layer is provided to improve the longevity of the thin-film device through preventing deterioration of the catalyst and/or optical sensing layers and improves the handleability of the device through preventing a user from coming into contact with the optical sensing and/or catalyst layers.

Control and reliability of e.g. hydrogen absorption is further achieved with the thin-film device of the invention by providing an optical sensing layer according to the invention.

Examples of coating layers are given in the Dutch Patent Application NL2010031, filed Dec. 20, 2012. Details, teachings and examples thereof are incorporated by reference.

The present optical sensing layers provide in an example for a range of hydrogen pressures between $1*10^{-1}$ Pa–$1*10^8$ Pa (at room temperature) to be detected accurately. It is noted that the present sensors may operate at room temperature and in addition can operate in a stable fashion at an elevated temperature (such as 120° C.). In comparison an optimal crystalline MgTi layer provides 1-2 orders of hydrogen pressure (~$1*10^2$ Pa–~$1*10^4$ Pa at 120° C.) to be detected accurately. The same applies to a single element Hf-detector, mutatis mutandis.

Desirable performance of the thin-film device of the invention in terms of control and reliability of hydrogen absorption can be achieved through either improvement separately or through the combination of improvements. Reliability relates particularly to reliability over time, such as tens of years, and with repeated use.

The invention also relates to a hydrogen sensor and to an electro-magnetic transformer comprising said hydrogen sensor.

The present invention provides a solution to one or more of the above mentioned problems and overcomes drawbacks of the prior art.

In the description and claims the term "on", as in a first layer on a second layer, includes the first layer being directly on the second layer, the first layer being above the second layer, or the first layer being above the second layer with an intermediate layer in between or with several intermediate layers in between, wherein the first layer may be partly or fully provided on the second layer.

Advantages of the present sensing material are detailed throughout the description.

DETAILED DESCRIPTION OF THE INVENTION

In an exemplary embodiment of the present tuneable hydrogen sensing device the hydrogen sensing material is provided as a thin layer, as a part of a thin layer, as nanoparticles, as microparticles, as a patterned nanosheet, as a nanowire, or a combination thereof.

In an exemplary embodiment of the present tuneable hydrogen sensing device the metal M in alloy $M_{1-y}A_x$ is selected from V, Nb, Ta, and alloys thereof, preferably Ta.

In an exemplary embodiment of the present tuneable hydrogen sensing device the at least one alloying element A in alloy $M_{1-y}A_x$ is selected from elements with a cubic cell, such as Pd, Ni, Ru, Rh, Fe, Co, and Pt, and combinations thereof, preferably Pd. Though cubic unit cells are preferred, pseudo-cubic cells could be considered.

In an exemplary embodiment of the present tuneable hydrogen sensing device the hydrogen sensing material has a thickness or cross-section in the range of 1.5-2000 nm, preferably 5-200 nm, more preferably 10-100 nm.

In an exemplary embodiment of the present tuneable hydrogen sensing device the hydrogenation of the sensing material is tuneable from $10^{-1}$ Pa (0.001 mbar)–$10^8$ Pa (1,000,000 mbar), at a temperature of 301K.

In an exemplary embodiment of the present tuneable hydrogen sensing device the hydrogen sensing material is provided on a substrate (10), or is incorporated in an embedding material, such as a matrix material, or is incorporated in a fibre, such as a fibre with a cladding 17, or is deposited on a fibre, or a combination thereof.

In an exemplary embodiment of the present tuneable hydrogen sensing device the hydrogen sensing material may further comprise at least one second alloying element $B_z$, wherein B is selected from metals, preferably from Pd, Ni, Pt, Ru, Rh, and combinations thereof, wherein hydrogenation of the sensing material is tuneable by changing an amount z of the at least one second alloying element in the alloy $M_{1-y}A_xB_z$, wherein the at least one alloying element B is present in an amount of 0.01-5 atom %.

In an exemplary embodiment the present tuneable hydrogen sensing device may further comprise (15) a protective layer provided on the sensing material, such as in the form of a layer, either directly or on an intermediate adhesive.

In an exemplary embodiment of the present tuneable hydrogen sensing device the protective layer comprises a polymer, such as polytetrafluoroethylene (PTFE), or polymethyl methacrylate (PMMA).

In an exemplary embodiment of the present tuneable hydrogen sensing device the protective layer has a thickness in the range of wherein the protective layer has a thickness in the range of 5-2000 nm, preferably 10-200 nm, more preferably 10-80 nm.

In an exemplary embodiment the present tuneable hydrogen sensing device may further comprise (14) a capping layer between the hydrogen sensing material and the protective layer.

In an exemplary embodiment of the present tuneable hydrogen sensing device the capping layer comprises one or more of Pd, Pt, Ag, Au, Ni, Cu, Ru, and Rh, preferably Pd and Au and optionally Cu.

In an exemplary embodiment of the present tuneable hydrogen sensing device the capping layer has a thickness in the range of 1.5-2000 nm, preferably 2-200 nm, more preferably 3-20 nm.

In an exemplary embodiment of the present tuneable hydrogen sensing device the intermediate adhesive 11,13 is selected from Ti, Cr, Au, or a combination thereof, and optionally wherein the intermediate adhesive has a thickness in the range of 1.5-400 nm, preferably 1.5-50 nm, more preferably 1.5-10 nm.

In an exemplary embodiment of the present tuneable hydrogen sensing device the protective layer and the capping layer are combined.

In an exemplary embodiment of the present tuneable hydrogen sensing device a concentration of the at least one alloying element A in the optical sensing layer varies continuously from 0.01 atom % to a maximum atom %, wherein the maximum atom % A is in a range from 10-35 atom %. As such a very large number of sensing "layers" can be formed within one sensor, each "layer" having a tuned hydrogen equilibrium pressure.

In an exemplary embodiment the present tuneable hydrogen sensing device may comprise at least one optical sensing layer, such as at least two layers, each layer comprising a sensing material with alloy $M_{1-y}A_x$.

In an exemplary embodiment the present tuneable hydrogen sensing device may comprise at least two sensing material domains, each domain comprising a different sensing material, wherein the domain has a size of 0.01-$10^8$ µm².

In an exemplary embodiment of the present tuneable hydrogen sensing device the device is for use in combination with photons with a wavelength in a range of 200-1200 nm.

In an exemplary embodiment of the present tuneable hydrogen sensing device the sensing material and capping layer exhibit optical interference at at least one given frequency.

Specific combinations considered are $Ta_{1-y}Pd_x$, $Ta_{1-y}Pt_x$, $Ta_{1-y}Ag_x$, $Ta_{1-y}Au_x$, $Ta_{1-y}Ni_x$, $Ta_{1-y}Cu_x$, $Ta_{1-y}Ru_x$, $Ta_{1-y}Rh_x$, $Nb_{1-y}Pd_x$, $Nb_{1-y}Pt_x$, $Nb_{1-y}Ag_b$, $Nb_{1-y}Au_x$, $Nb_{1-y}Ni_x$, $Nb_{1-y}Cu_x$, $Nb_{1-y}Ru_x$, $Nb_{1-y}Rh_x$, $V_{1-y}Pd_x$, $V_{1-y}Pt_x$, $V_{1-y}Ag_x$, $V_{1-y}Au_x$, $V_{1-y}Ni_x$, $V_{1-y}Cu_x$, $V_{1-y}Ru_x$, and $V_aRh_x$.

Preferably 1−y∈[0.85, 0.999] and x∈[0.001, 0.15]. Preferably x∈[0.01, 0.10]. Further specific combinations considered are $Ta_{1-y}Pd_xNi_z$, $Ta_{1-y}Pt_xNi_z$, $Ta_{1-y}Ag_xNi_z$, $Ta_{1-y}Au_xNi_z$, $Ta_{1-y}Cu_xNi_z$, $Ta_{1-y}Ru_xNi_z$, $Ta_{1-y}Rh_xNi_z$, $Ta_{1-y}Ni_xPd_z$, $Ta_{1-y}Pt_xPd_z$, $Ta_{1-y}Ag_xPd_z$, $Ta_{1-y}Au_xPd_z$, $Ta_{1-y}Cu_xPd_z$, $Ta_{1-y}Ru_xPd_z$, $Ta_{1-y}Rh_xPd_z$, $Ta_{1-y}Pd_xPt_z$, $Ta_{1-y}Ni_xPt_z$, $Ta_{1-y}Ag_xPt_z$, $Ta_{1-y}Au_xPt_z$, $Ta_{1-y}Cu_xPt_z$, $Ta_{1-y}Ru_xPt_z$, $Ta_{1-y}Rh_xPt_z$, $Ta_{1-y}Pd_xRu_z$, $Ta_{1-y}Ni_xRu_z$, $Ta_{1-y}Ag_xRu_z$, $Ta_{1-y}Au_xRu_z$, $Ta_{1-y}Cu_xRu_z$, $Ta_{1-y}Pt_xRu_z$, $Ta_{1-y}Rh_xRu_z$, $Ta_{1-y}Pd_xRh_z$, $Ta_{1-y}Ni_xRh_z$, $Ta_{1-y}Ag_xRh_z$, $Ta_{1-y}Au_xRh_z$, $Ta_{1-y}Cu_xRh_z$, $Ta_{1-y}Pt_xRh_z$, and $Ta_{1-y}Ru_xRh_z$.

Preferably 1−y∈[0.85, 0.999], x∈[0.001, 0.15], and z∈[0.001, 0.15]. Preferably x∈[0.01, 0.10].

The invention will hereafter be further elucidated through the following examples which are exemplary and explanatory of nature and are not intended to be considered limiting of the invention. To the person skilled in the art it may be clear that many variants, being obvious or not, may be conceivable falling within the scope of protection, defined by the present claims.

FIGURES

FIG. 1 shows a schematic set-up of the present device.

Figure 2:
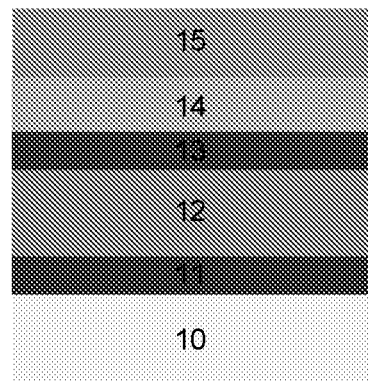

FIG. 2 shows a stack of layers, comprising a substrate 10, a sensing layer 12, an optional capping layer 14, and an optional protection layer 15.

Figure 3:
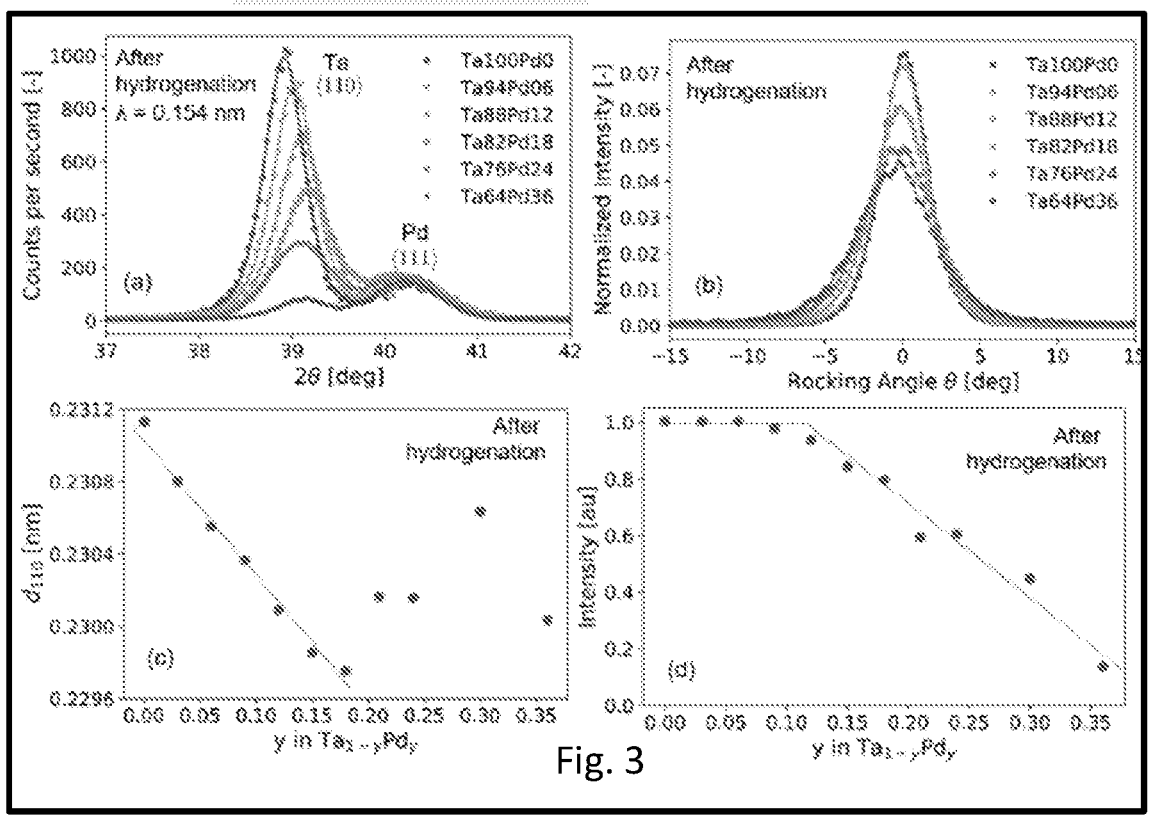

FIG. 3: Ex-situ XRD results of the 40 nm $Ta_{1-y}Pd_y$ thin films with a 4 nm Ti adhesion layer and capped with a 10 nm Pd layer after exposure of the thin films to hydrogen and measured in air.

FIG. 4a-c: Partial hydrogen pressure and temperature dependence of the optical transmission T of 40 nm $Ta_{1-y}Pd_y$ sensing layers measured relative to the optical transmission of the as-prepared state (T prep).

FIGS. 5a-c show changes of the green light optical transmission T of the 40 nm $Ta_{1-y}Ru_y$ sensing layers. The optical transmission is measured as a function of time and relative to the transmission of the as-prepared film (T prep). The film was exposed at T=28° C. to various increasing and decreasing pressure steps of (a) $1.5 \times 10^{-1} \leq PH_2 \leq 1.0 \times 10^{+2}$ Pa, (b) $2 \times 10^{+2} \leq PH_2 \leq 4 \times 10^{+5}$ Pa, and c) $5.5 \times 10^{+3} \leq PH_2 \leq 1.0 \times 10^{+6}$ Pa. The dashed lines indicate levels of the same transmission (top panel) and pressure (bot-tom panel).

FIG. 6 shows the partial hydrogen pressure dependence of the green light optical transmission T of the 40 nm $Ta_{1-y}Ru_z$ sensing layers measured relative to the optical transmission of the as-prepared state (T prep) at 28° C. Each data-point corresponds to the optical transmission after exposing the film for at least 20 min to a constant pressure of $P_{H2}=10^{-1}$-$10^{+6}$ Pa, where the closed data points correspond to increasing pressure steps, and the open ones to decreasing pressure steps.

Figure 7A:
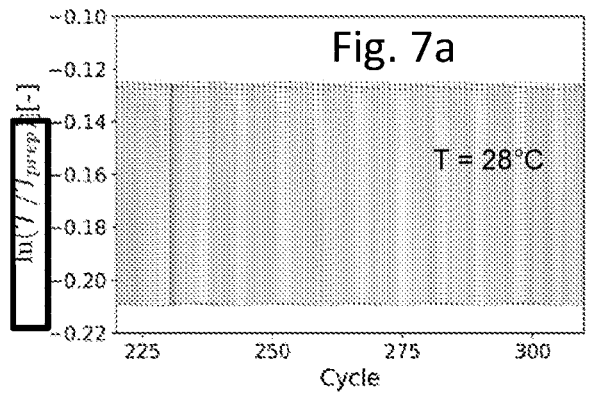

FIG. 7a,b: Stability of a 40 nm $Ta_{0.88}Pd_{0.12}$ thin film with a 4 nm Ti adhesion layer capped with a 10 nm $Pd_{0.6}Au_{0.35}Cu_{0.05}$ layer that is covered with a 30 nm PTFE layer.

Figure 8C:
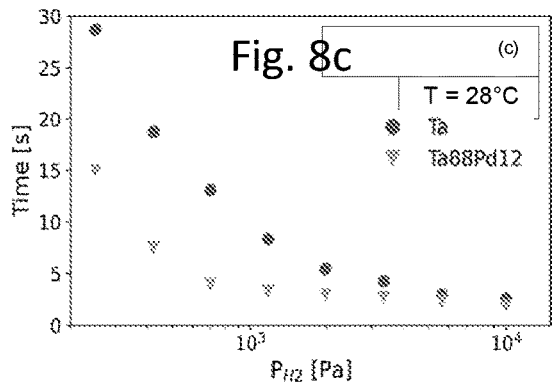
Figure 8A:
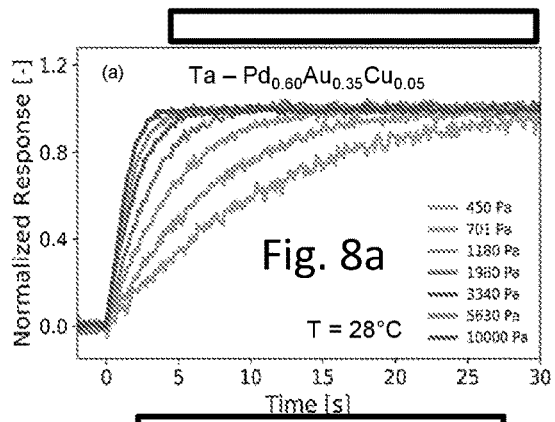
Figure 8B:
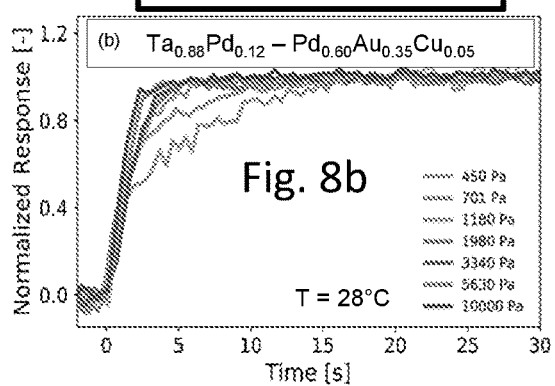

FIG. 8a-c: Adsorption kinetics of a 40 nm $Ta_{0.88}Pd_{0.12}$ thin film with a 4 nm Ti adhesion layer capped with a 10 nm $Pd_{0.6}Au_{0.35}Cu_{0.05}$ layer that is covered with a 30 nm PTFE layer.

Figure 9A:
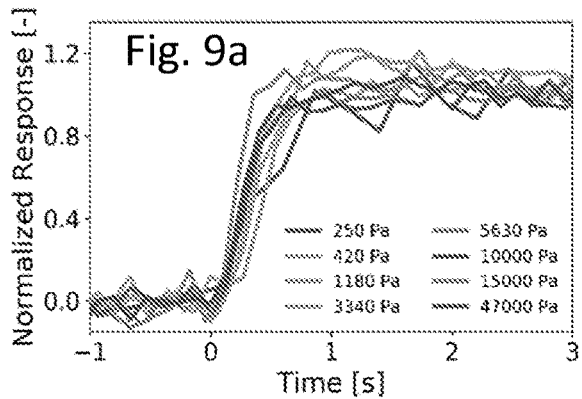
Figure 9B:
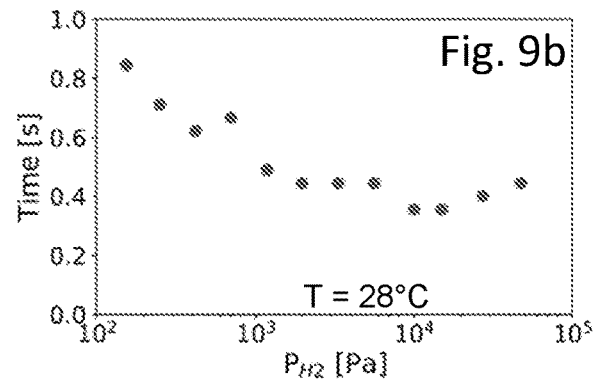

FIG. 9a-b: Comparison of adsorption kinetics between a 40 nm Ta and a 40 nm $Ta_{0.88}Pd_{0.12}$ thin film that both have a 4 nm Ti adhesion layer and are capped with a 10 nm $Pd_{0.6}Au_{0.35}Cu_{0.05}$ layer at T=28 C.

DETAILED DESCRIPTION OF FIGURES

In the figures:

1 tunable hydrogen sensing device
10 substrate/support
11 optional substrate-sensing layer adhesion material
12 hydrogen sensing material
13 optional capping layer-sensing layer adhesion material
14 capping layer
15 protection layer
16 optical fiber
17 cladding of fiber
18 hydrogen sensing material read-out system
22 splitter
23 CCD camera

EXPERIMENTAL 1.1 Sample Preparation

The $Ta_{1-y}Pd_y$ samples are composed of a 4 nm titanium adhesion layer, a 40 nm $Ta_{1-y}Pd_y$ layer and a 10 nm cap layer to catalyze the hydrogen dissociation and re-combination reaction and prevent the film from oxidation. As a cap layer, we have both used a Pd and a $Pd_{0.6}Au_{0.35}Cu_{0.05}$ covered with a 30 nm PTFE layer to reduce response times. The layers are deposited on 10*10 mm² quartz substrates (thickness of 0.5 mm and surface roughness <0.4 nm) in 0.3 Pa of Ar by magnetron sputtering in n ultrahigh vacuum chamber (AJA Int.) with a base pressure of $10^{-10}$ Pa. PTFE was deposited by radiofrequency magnetron sputtering in 0.5 Pa of Ar. The Ta target was pre-sputtered for at least 240 min to avoid possible contamination from the tantalum oxide and nitride layers at the surface of the target. We note that for commercial manufacturing one can use alloy targets, and that alloys of $Ta_{1-y}Pd_y$ are, even at low concentrations of Pd, not susceptible to nitration and oxidation. This is one of the advantages of the present material over single-element sensing materials.

1.2 Structural Measurements

Ex-situ X-ray diffraction (XRD) measurements were performed with a Bruker D8 Discover in combination with a Cu X-ray source. In-situ XRD measurements were performed with a Bruker D8 Advance in combination with a Co X-ray source and an Anton Paar XRK 900 reactor chamber.

1.3 Optical Measurements

The white-light optical transmission of the Pd-capped samples were measured using hydrogenography with a Sony DXC-390P three charge-coupled device (3CCD) color video camera and a maximum acquisition frequency of 0.5 Hz. The partial hydrogen pressures of $10^{-1}<PH_2<10^{+6}$ Pa are obtained by using 0.1%, 4% and 100% $H_2$ in Ar gas mixtures. The measurements on the $Pd_{0.6}Au_{0.35}Cu_{0.05}$ PTFE capped samples were performed using a similar set-up in which the 3CCD camera was re-placed by an Imaging Source 1/2.5" Aptina CMOS 2592×1944 pixel monochrome camera with an Edmunds Optics 55-906 lens.

2. Structural Measurements

FIG. 3 shows ex-situ XRD results of the 40 nm $Ta_{1-y}Pd_y$ thin films with a 4 nm Ti adhesion layer and capped with a 10 nm Pd layer after exposure of the thin films to hydrogen and measured in air. FIG. 3(a) shows diffractograms of the $Ta_{1-y}Pd_y$ thin films. In this figure, the continuous lines represent fits of two pseudo-Voigt functions to the experimental data. In FIG. 3(b) Rocking curves of the $Ta_{1-y}Pd_y$ thin films around the $Ta_{1-y}Pd_y$ <110> peak are shown. FIG. 3(c) shows the Pd doping dependence of the $d_{110}$-spacing in $Ta_{1-y}Pd_y$. FIG. 3(d) displays the Pd doping dependence of the total intensity of the <110> diffraction peak in $Ta_{1-y}Pd_y$ in which the effect of both the changing amplitude and width are incorporated. The intensity is scaled to the intensity of the Ta sample. In this figure, the dashed lines serve as guides to the eye.

Inventors also employ in-situ XRD to study the structural response of $Ta_{1-y}Pd_y$ to hydrogen. The objective of these measurements is to determine whether the various ordered and disordered cubic and orthorhombic phases found in bulk $TaH_h$ for various values of h are present at low temperatures (e.g. below the critical temperature of Tc=61° C.) in the present $Ta_{1-y}Pd_y$ nanosized thin films. If this would have been the case, it would make the thin films unsuitable for room-temperature hydrogen sensing as a result of the sizable hysteresis involved in the first-order transitions between these various phases.

3. Optical Response of the Sensing Material

For a material to be suitable for optical hydrogen sensing, the optical properties should change considerably and uniformly with the application of a hydrogen pressure. To evaluate this, inventors perform white-light optical transmission measurements of the Pd-capped $Ta_{1-y}Pd_y$ thin films by stepwise exposing the film to a series of increasing and decreasing hydrogen pressures between $10^{-1} < PH_2 < 10^{+6}$ Pa. It is noted that $Ta_{0.5}Pd_{0.5}$ does not show any optical response in the investigated pressure range and provides similar adhesion conditions, ensuring that the optical response of the Pd layer mimics the one on top of the film of interest.

The levels of transmission are well-defined and stable for a given partial hydrogen pressure, and, importantly, free of any hysteresis: the optical transmission is, in accordance with the in-situ XRD measurements, the same after increasing and decreasing pressure steps.

The optical transmission measurements are summarized in FIG. 4. It shows the measurements performed for different pressures between $1.0\ 10^{-1} < PH_2 < 1.0\ 10^{+6}$ Pa, for different Pd concentrations of $0.0 \le y \le 0.36$, and for 28, 60, 90 and 120° C. In this figure, the pressure-transmission-isotherms (PTIs) are plotted, where each closed data-point corresponds to the optical transmission obtained after exposing the film for at least one hour to a constant pressure after an increase in pressure, and the open points to decreasing pressure steps.

The optical transmission measurements are summarized in FIG. 4. It shows the measurements performed for different pressures between $1.0\ 10^{-1} < PH_2 < 1.0\ 10^{+6}$ Pa, for different Pd concentrations of $0.0 \le y \le 0.36$, and for 28, 60, 90 and 120° C. In this figure, the pressure-transmission-isotherms (PTIs) are plotted, where each closed data-point corresponds to the optical transmission obtained after exposing the film for at least one hour to a constant pressure after an increase in pressure, and the open points to decreasing pressure steps. The right axis indicates h in $Ta_{1-y}Pd_yH_h$ as based on the scaling between the optical response and the hydrogen content obtained using in-situ neutron reflectometry measurements. Additional optical measurements on a $Ta_{1-y}Ru_y$ sensing layer are provided in FIGS. 5 and 6.

For safety as well as other applications a short response time of a hydrogen sensor is crucial, especially for hydrogen pressures close to the explosive limit in air of 4%. Inventors performed room temperature response time measurements for the $Ta_{0.88}Pd_{0.12}$ sample capped with a 10 nm $Pd_{0.6}Au_{0.35}Cu_{0.05}$ layer that is covered with a 30 nm PTFE layer which are shown in FIG. 8-9). While other thin film materials re-ported so far often have the disadvantage that the response times are especially at room temperature too long for most applications, the room temperature response time of the 40 nm $Ta_{0.88}Pd_{0.12}$ based thin film is smaller than 1 s in the entire pressure window of $PH_2 = 10^{+2} < PH_2 < 10^{+5}$ (measured e.g. at 250 Pa, 420 Pa, 1180 Pa, 3340 Pa, 5630 Pa, 10000 Pa, 15000 Pa, and 47000 Pa. This corresponds to a hydrogen concentration range of 0.1 to 100% under ambient conditions. As shown in FIG. 9, the introduction of Pd in Ta enhances the kinetics. In fact, these response times are shorter than other hydrogen sensors including those based on metal-hydride nanoparticles.

Figure 7B:
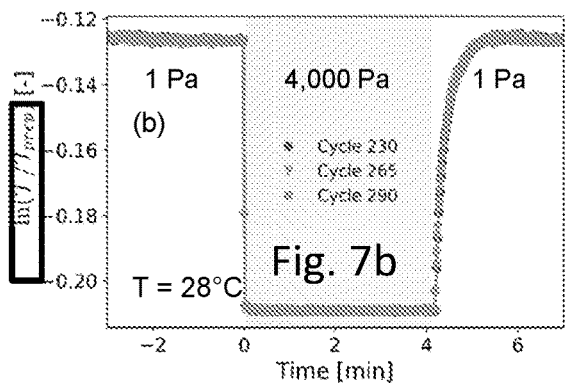

Another requirement to hydrogen sensors is good reproducibility and long-term stability. To illustrate the stability of the sensor response, inventors exposed the thin film to 310 cycles of hydrogen between $PH_2 = 1.0$ and $4.0\ 10^{+3}$ Pa at T=28° C. FIG. 7 demonstrates that no change is behavior or response was observed.

The invention claimed is:

1. A tuneable hydrogen sensing device allowing controlled and reliable, hysteresis free, measurement of an amount of hydrogen comprising:
   a hydrogen sensing material (12), the hydrogen sensing material comprising an alloy $M_{1-y}A_xB_z$, wherein y=x+z, and wherein $z \ge 0$, wherein the metal M is selected from Group V elements, and at least one alloying element A being selected from elements with a cubic unit cell, and combinations thereof, wherein hydrogenation of the sensing material is tuneable by changing an amount x of the at least one alloying element in the alloy $M_{1-y}A_xB_z$, wherein the at least one alloying element A is present in an amount of x=0.01-35 atom %; and
   a hydrogen sensing material read-out system (20), wherein the read-out system is selected from optical read-out systems, dielectric read-out systems, electromagnetic read-out systems, an electrical voltage detector, an electrical resistance detector, and a transistor, and combinations thereof.

2. The tuneable hydrogen sensing device according to claim 1, wherein the hydrogen sensing material is provided as one of a thin layer, a part of a thin layer, nanoparticles, microparticles, a patterned nanosheet, a nanowire, and a combination thereof.

3. The tuneable hydrogen sensing device according to claim 1, wherein the hydrogen sensing material is provided as one of on a substrate (10), on an adhesion layer (11) which is provided on the substrate (10), is incorporated in an embedding material, is incorporated in a fibre (16), is deposited on a fibre (16), and a combination thereof.

4. The tuneable hydrogen sensing device according to claim 1, wherein the metal M is selected from V, Nb, Ta, and alloys thereof, and
   wherein the hydrogen sensing material has one of a thickness and a cross-section in the range of 1.5-2000 nm.

5. The tuneable hydrogen sensing device according to claim 1, wherein the hydrogen sensing material further comprises at least one second alloying element $B_z$, wherein B is selected from metals Pd, Ni, Pt, Ru, Rh, and combinations thereof, wherein hydrogenation of the sensing material is tuneable by changing an amount z of the at least one second alloying element in the alloy $M_{1-y}A_xB_z$, wherein the at least one alloying element B is present in an amount of 0.01-5 atom %.

6. The tuneable hydrogen sensing device according to claim 1, further comprising (14) a capping layer between the hydrogen sensing material and a protective layer,
   wherein the capping layer comprises at least one of Pd, Pt, Ag, Au, Ni, Cu, Ru, and Rh, and wherein the capping layer has a thickness in the range of 1.5-2000 nm.

7. The tuneable hydrogen sensing device according to claim 1, further comprising (15) a protective layer provided on the sensing material,
   wherein the protective layer comprises a polymer.

8. The tuneable hydrogen sensing device according to claim 1, comprising at least one intermediate layer (11, 13), and
   wherein the intermediate layer (11, 13) each individually is selected from Ti, Cr, Au, and a combination thereof, and wherein the intermediate layer (11, 13) each individually has a thickness in the range of 1.5-400 nm.

9. The tuneable hydrogen sensing device according to claim 1, wherein the hydrogenation of the sensing material is tuneable from $10^{-1}$ Pa (0.001 mbar)-$10^8$ Pa (1,000,000 mbar), at a temperature of 301K.

10. The tuneable hydrogen sensing device according to claim 6, wherein a/the protective layer and a/the capping layer are combined.

11. The tuneable hydrogen sensing device according to claim 1, wherein a concentration of the at least one alloying element A in the optical sensing layer varies continuously from 0.01 atom % to a maximum atom %, wherein the maximum atom % A is in a range from 10-35 atom %.

12. The tuneable hydrogen sensing device according to claim 1, comprising at least one optical sensing layer, each layer comprising a sensing material.

13. The tuneable hydrogen sensing device according to claim 1, comprising at least two sensing material domains, each domain comprising a different sensing material, wherein the domain has a size of 0.01-$10^8$ µm$^2$.

14. The tuneable hydrogen sensing device according to claim 1, wherein the device is for use in combination with photons with a wavelength in a range of 200-1200 nm.

15. The tuneable hydrogen sensing device according to claim 1, wherein the sensing material and capping layer exhibit optical interference at at least one given frequency.

16. A sensor comprising at least one device of claim 1, comprising an optical transmitter, wherein the sensing layer is located at a top of the optical transmitter and wherein the sensing layer is located at a longitudinal side of the optical transmitter.

17. A device comprising a sensor according to claim 16 for monitoring one of a hydrogen pressure and a hydrogen concentration, wherein the device is selected from an electro-magnetic transformer, a hydrogen storage device, and a battery.

18. An apparatus for detecting hydrogen comprising a sensor with a sensing material, the sensor being located at one of a longitudinal side of an optical transmitter, and a top side of an optical transmitter, the optical transmitter comprising
 a central transmitting element, wherein the central transmitting element is a quartz core,
 a tuneable hydrogen sensing material according to claim 1, the hydrogen sensing material comprising an alloy $M_{1-y}A_xB_z$, wherein y=x+z, and wherein z≥0, wherein the metal M is selected from Group V elements, and at least one alloying element A being selected from elements with a cubic unit cell, and combinations thereof, wherein hydrogenation of the sensing material is tuneable by changing an amount x of the at least one alloying element in the alloy $M_{1-y}A_xB_z$, wherein the at least one alloying element A is present in an amount of x=0.01-35 atom %, and
 a spectrometer.

19. The tuneable hydrogen sensing device according to claim 1, wherein the at least one alloying element A is selected from Pd, Ni, Pt, Ru, Rh, and combinations thereof.

\* \* \* \* \*